(12) United States Patent
Messier et al.

(10) Patent No.: US 8,071,713 B2
(45) Date of Patent: Dec. 6, 2011

(54) IODINATED RESIN MANUFACTURING PROCESS AND PRODUCT

(75) Inventors: Pierre J. Messier, Quebec (CA);
Jean-Pierre S. Louis, Prevost, CA (US);
David Ohayon, Dollard-Des-Ormeaux (CA)

(73) Assignee: TrioMed Innovations Corp., South Burlington, VT (US)

( * ) Notice: Subject to any disclaimer, the term of this patent is extended or adjusted under 35 U.S.C. 154(b) by 131 days.

(21) Appl. No.: 12/586,504

(22) Filed: Sep. 22, 2009

(65) Prior Publication Data

US 2010/0074858 A1 Mar. 25, 2010

Related U.S. Application Data

(60) Provisional application No. 61/192,775, filed on Sep. 22, 2008.

(51) Int. Cl.
*C08F 6/00* (2006.01)
*C08J 3/00* (2006.01)

(52) U.S. Cl. ........................................ 528/481; 528/480

(58) Field of Classification Search .................. 528/480, 528/481
See application file for complete search history.

(56) References Cited

U.S. PATENT DOCUMENTS

| | | |
|---|---|---|
| 3,923,665 A | 12/1975 | Lambert |
| 4,017,407 A | 4/1977 | Cantor et al. |
| 4,094,967 A | 6/1978 | Gilbert |
| 4,187,183 A | 2/1980 | Hatch |
| 4,381,380 A | 4/1983 | Le Veen et al. |
| 4,469,826 A | 9/1984 | Carlick et al. |
| 4,483,771 A | 11/1984 | Koch |
| 4,538,158 A | 8/1985 | Warszawski |
| 4,584,192 A | 4/1986 | Dell et al. |
| 4,668,510 A | 5/1987 | Shetty |
| 4,798,870 A | 1/1989 | Lyle |
| 5,219,580 A | 6/1993 | Torres et al. |
| 5,236,703 A | 8/1993 | Usala |
| 5,326,567 A | 7/1994 | Capelli |
| 5,370,534 A | 12/1994 | Wolf et al. |
| 5,431,908 A | 7/1995 | Lund |
| 5,607,683 A | 3/1997 | Capelli |
| 5,618,799 A | 4/1997 | Inagi et al. |
| 5,639,452 A | 6/1997 | Messier |
| 5,662,913 A | 9/1997 | Capelli |
| 6,106,773 A | 8/2000 | Miekka et al. |
| 6,370,694 B1 | 4/2002 | Michelson |
| 6,562,885 B1 * | 5/2003 | Moorehead et al. ............ 524/80 |
| 2006/0251879 A1 | 11/2006 | Messier |

\* cited by examiner

*Primary Examiner* — Terressa Boykin
(74) *Attorney, Agent, or Firm* — Hoffmann & Baron, LLP; Besty Kingsbury Dowd, Esq.

(57) ABSTRACT

The invention provides a novel method for manufacturing iodinated resin particulates that have widespread utility as disinfectants. The invention also provides novel iodinated demand disinfectant iodinated resins that have superior properties than resins known in the art. The novel manufacturing process of the current invention is highly efficient and environmentally friendly and is conducted without the presence of water. Additionally, the manufacturing process produces iodinated resins that have better overall biological performance than resins produced by prior art methods owing to higher degrees of iodine in the manufactured resin particulates and higher degrees of uniformity of iodine content when comparing particulate to particulate.

19 Claims, No Drawings

IODINATED RESIN MANUFACTURING PROCESS AND PRODUCT

CROSS-REFERENCE TO RELATED APPLICATIONS

This application claims the benefit of priority to U.S. Provisional Application No. 61/192,775, filed on Sep. 22, 2008, the content of which is incorporated by reference.

BACKGROUND

Demand disinfectant iodinated resins have been used in a variety of applications. For instance, iodinated resins may be used to sterilize fluids such as water, air, blood and other bodily secretions by devitalizing microorganisms such as fungi, protozoan, bacteria and viruses that may be present in the fluid. Additionally, iodinated resins can be used in wound dressings, disinfectants, filters, clothing, fibers, facemasks, polymers, non-polymeric structures and coatings.

Numerous manufacturing processes for making demand disinfectant iodinated resins are disclosed in the prior art. U.S. Pat. No. 5,639,452 to Messier, the content of which is incorporated herein by reference, discloses a disinfectant substance comprising iodine impregnated ion exchange resin and a process for the preparation thereof. The Messier patent discloses that this disinfectant is a demand-type broad spectrum resin-polyiodide disinfectant useful in sterilizing fluids, and particularly a polyiodide disinfectant in which the iodine is more tenaciously associated with the resin than with previously known disinfectants, such that it leaves behind non-detectable or otherwise acceptable residual diatomic iodine in treated fluids. The demand disinfectant iodinated resins disclosed in Messier are generally formed by contacting a strongly basic anionic resin with an aqueous solution of iodine and potassium iodide under conditions of high temperature and pressure. Iodinated resin beads (Triosyn®) are made by Triosyn Research Inc., a division of Triosyn Corporation of Vermont, USA.

U.S. Pat. No. 5,431,908 to Lund also teaches a method of preparing halide-impregnated ion exchange resins useful in purifying fluids such as water. The method involves circulating an effective amount of polyhalide salt carrier solution between an effective amount of elemental iodide and a strong base anion exchange resin until all of the resin is converted to the polyhalide form.

The processes disclosed in Messier and Lund are useful in preparing iodinated resin granules or beads with diameters ranging from 0.2 mm (200 microns) to 0.8 mm (800 microns). However, smaller particulates are required for the production of some filters, polymeric or non-polymeric extrusions, wound dressings, fibers and coatings Moreover, use of iodinated resins in coatings and in aerosols requires smaller particulates. It is possible to produce small iodinated resin particulates of the desired size by grinding the beads produced by the method described in Messier. In addition, U.S. Pat. No. 6,562,885, to Moorehead, the content of which is incorporated herein by reference, discloses a method of manufacturing smaller iodinated resin particulates, on the scale of 0.1-300 microns. Moorehead starts with iodinated resin beads, as prepared in Messier, and grinds them into smaller particulates. After selecting particulates of the appropriate size, the particulates may be re-iodinated by contacting them with an aqueous solution of iodine and potassium iodide under conditions of high temperature and pressure.

The methods described above for producing micronized iodinated resin particulates have several disadvantages. The pieces of particulate iodinated resin formed following the grinding of the larger iodinated resin beads have different iodine content because the large beads cannot be homogeneously iodinated from the surface to the core of the sphere of the bead. In the larger beads, there is less iodine in the center of the bead than on the edges of the bead. As a result, the individual particulates, after grinding of the larger resin bead, have differential amounts of iodine. Although the particulates can be re-iodinated, as described in Moorehead, the re-iodination process does not produce uniformly iodinated particulates. While the iodine content of the initially less impregnated particulates is increased, the iodine content of the particulates that were already optimal prior to re-iodination is increased as well. Additionally, the process results in a considerable amount of iodine waste, which is environmentally toxic.

Being that the percent iodine content of a resin determines the toxicological properties and the biocidal properties thereof, such nonuniformity translates into a large fluctuation of the biocidal performances of individual particulates. As a result, when the particulates are incorporated into filters, polymeric extrusions or coatings, for example, the resultant product (e.g., filter, wound dressing or wipe) may not behave uniformly. Consequently, if iodinated resin particulates are incorporated into a filter, it is possible that microorganisms migrating through areas of the material containing particulates of low iodine content will not be devitalized while microorganisms migrating through areas of the filter containing areas of high iodine content will be devitalized. Moreover, being that the particles are dispersed in a medium having an area much larger than the iodinated resin particulates, different areas of the medium may have different toxicological properties.

In addition to problems with nonuniformity described in the preceding paragraphs, the methods described in Messier, Lund and Moorehead are time-consuming, technologically challenging and costly. For instance, methods described in Messier and Moorehead necessitate the use of a step for iodine impregnation with requires water or other liquids, or batch blending. In particular, prior art methods require the use of an aqueous sludge of iodine and potassium iodide. Working with such a sludge is complicated, particularly when dealing with small resin particulates. Moreover, in order to obtain a dry iodinated powder to be used in filters, coatings, polymeric and non-polymeric extrusions, the additional step of drying the water content is required. Generating smaller particulates is particularly challenging. Using the Moorehead process, for instance, requires two iodination steps, one to produce the larger beads and one to re-iodinate the smaller particulates after grinding. Hence, the batch process and drying steps must be performed twice. When a specific range of particulate size is required a sieving step is also required. Accordingly, the multiple manufacturing steps are extensive and cost-prohibitive.

Furthermore, the prior art manufacturing processes may have negative environmental consequences owing to the loss of iodine to the environment. Processes requiring multiple iodination steps are particularly unfriendly to the environment. Additionally, the use of water in the prior art processes generates considerable toxicological waste because fluid containing iodine are generated.

Hence, there exists a need to develop a new manufacturing process to generate iodinated resins that is technologically simpler, less costly, yielding a more biologically potent and more environmentally friendly resin. Additionally, there exists a need to generate small iodinated resin particulates that have a uniform content of iodine and thereby can be applied to antimicrobial products including filters, coatings and wound dressings.

SUMMARY OF INVENTION

In accordance with these objectives, a new manufacturing process for generating halogenated (e.g., iodinated) resin particulates (e.g., beads and powders) has been developed. The novel manufacturing process uses less raw materials (iodine) which decreases the cost of the end products, is environmentally friendly and produces iodinated resins with superior iodine content then processes described in the prior art, which translates to better antimicrobial performance.

One aspect of the present invention is a manufacturing process for producing an iodinated resin comprising the steps of providing a quantity of iodine, providing a quantity of milled anionic dried resin, mixing the micronized iodine and milled anionic dried resin in a vessel for a time suitable to form an intimate mixture, placing the container with the mixture in a high temperature/high pressure heating vessel for a time sufficient to allow the iodine to absorb or become impregnated in said resin, and recovering the iodinated resin.

Another aspect of the present invention is a method of forming iodinated rein particulates without using a liquid.

Another aspect of the present invention is an improved iodinated resin that is produced by providing a quantity of iodine, providing a quantity of milled anionic dried resin, mixing the micronized iodine and milled anionic dried resin in a vessel for a time suitable to form an intimate mixture, placing the container with the mixture in a high temperature/ high pressure heating vessel for a time sufficient to allow the iodine to absorb or become impregnated in said resin, and isolating the iodinated resin.

Yet another aspect of the present invention is a mixture of iodinated resin particulates having a particle size substantially in the range of 0.1-300 microns where all the particles would have substantially the same iodine load.

Yet another aspect of the present invention is using the iodinated resin particles produced in accordance with the present invention as an antimicrobial agent in filters, coatings, woven and non-woven materials, wound dressings, aerosols, disinfectants, and blood transfusion devices.

DETAILED DESCRIPTION OF INVENTION

The invention provides a novel method for manufacturing activated resin particulates that have widespread utility in a variety of disinfectants and antimicrobial and antiviral products. The invention also provides novel activated demand disinfectant iodinated resins that have superior properties than resins known in the art. Preferably, the iodinated resin is an iodinated resin. The novel manufacturing process of the current invention is highly efficient and environmentally friendly. Additionally, the manufacturing process produces antimicrobial iodinated resins that have better overall performance (higher efficacy) than resins produced by prior art methods owing to higher degrees of iodine in the manufactured resin particulates and higher degrees of uniformity of iodine content when comparing particulate to particulate.
Manufacturing Process In one embodiment of the present invention, the iodinated resin may be prepared generally as follows:
  i. Obtain micronized anionic resin through a jet-milling procedure or other acceptable method.
  ii. Weigh out a quantity of the milled anionic dry resin having particle sizes ranging from 0.1 micron to 300 microns.
  iii. Weigh out a quantity of solid iodine.
  iv. Place the solid mixture in a noncorrosive heatable vessel and cap it.
  v. Place the heatable vessel in a mixer for a time period suitable to form an intimate mixture.
  vi. Once mixing is complete, place the noncorrosive heatable vessel in a high temperature/high pressure heating vessel for heating for a period of time sufficient to allow the iodine to absorb or become impregnated in said resin.
  vii. When heating is complete, remove the noncorrosive heatable vessel from the high temperature/high pressure heating vessel and cool.
  viii. Once cooled, pack and store the final product.

The milled dry anionic resin may be obtained through a jet-milling process. Two preferred jet-milling systems are the 400AAG and 400TTG manufactured by Hosokawa Micron Group. In the jet-milling process, an anionic exchange resin, preferably in bead or granule form, is grinded down to the appropriate size. These jet-milling systems are capable of producing anionic dry resin particulates with sizes as small as 5 microns or less with a precise particulate size range distribution. Percent distribution of particle sizes can be adjusted to required needs. The anionic resin particulates may have particular moisture content in the form of bound water. For instance, the anionic resin particulates may have moisture content between 3%-40%.

The starting anionic resin may be any polymer allowing for iodine impregnation, and absorption of iodine. For example, the resin may be a strong-base or weak-base anionic exchange resin such as those described in U.S. Pat. No. 5,639,452. In a preferred embodiment, the anionic resin is a strong-base anionic exchange resin. Strong-base ion exchange resins include resins that contain strongly basic groups such as quaternary ammonium, sulfonium or phosphonium groups. Commercially available quaternary ammonium anion exchange resins which can be used in accordance with the present invention include in particular, Amberlite IRA-401 S, Amberlite IR-400 (Cl$^-$), Amberlite IR-400 (OH$^-$), Amberlite IR-402 (Cl$^-$), etc., (from Rohm & Hass) which may be obtained in granular form. These resins may for example, contain quaternary ammonium exchange groups which are bonded to styrene-divinyl benzene polymer chains.

After weighing out the desired quantity of milled anionic dry resin, the milled anionic dry resin is placed in a heatable noncorrosive vessel. The desired quantity of iodine is then placed in the noncorrosive heatable vessel and the vessel is capped. The iodine is preferably micronized (pre-grinded) iodine. The quantity of the milled anionic dry resin and micronized iodine is selected from the desired end product specifications on a weight bases.

The heatable noncorrosive vessel containing the mixture of anionic resin and iodine is then placed in a mixer for a period of time sufficient to form an intimate mixture of the anionic resin and the iodine. For example, the anionic resin and the iodine may be placed in a rotary mixture for a period of time between 10 minutes to 20 hours, preferably between 15 and 25 minutes. Mixing can be accomplished in the presence or absence of heat and elevated pressure.

Once mixing is complete, the noncorrosive vessel containing the mixture is placed in a high temperature/high pressure heating vessel and heated. Pressures ranging from 1 to 300 psi and temperatures ranging from 65° C. to 200° C. are suitable. A preferred range is 100° C. to about 135° C. at a pressure of about 10 psi to about 30 psi for about 10 to 20 minutes. A particularly preferred embodiment is heating is done at 15 psi at a temperature ranging from 105° C. to 110° C. for approximately 15 minutes. These conditions allow for effective ion-exchange between the milled anionic dry resin and the iodide/iodine. The ion-exchange process in which the milled anionic dry resin is converted to an iodinated resin is referred to as conversion. Following conversion, either diatomic iodine or triiodide ($I_3^-$) is absorbed or impregnated in the resin. The term "triiodide" refers to a substance or a complex containing three iodine atoms and which has a valence of −1. Iodine absorbed on the resin may be chemically converted to triiodide.

To facilitate conversion of diatomic iodine to triiodide, solid potassium iodide (KI) may be added, but is not mandatory, to the mixture prior to mixing and pressurizing. Potassium iodide or physically/chemically generated iodide reacts with diatomic iodine to generate triiodide. During the conversion step, the triodide exchanges with the anionic component of the anionic dry resin.

The iodinated resin particulates may be isolated following the conversion step and subsequent cooling. If desired, the particulates may be sieved to get a particular range of sizes. Sizes of the iodinated resin particulates range from about 0.1 micron to about 300 microns. Preferred sizes are dependent on the nature of the end product that will encompass the iodinated rein particulates. For example non-woven extrusion for melt blown would prefer a 4-5 micron particulate, and a spun bound would prefer a 10 micron particulate. As discussed below, the iodinated resin particulates formed from the inventive manufacturing process have a uniform quantity of iodine content from particulate to particulate. The iodine content in the individual particulates may range from about 10% to about 70% depending upon their ultimate use in antimicrobial-based products. A preferred range of iodine content of the iodinated resin particulates in between 45%-55%.

The manufacturing process described above offers significant advantages over prior art methods used to generate iodinated resins. The process eliminates the numerous manipulation of materials utilized in prior methods and concentrates all manufacturing steps into one single processing step. One advantage of the present method is that the use of liquids such as water are eliminated. As discussed in the Background section, water tends to complicate the process, particularly when dealing with small particulates. For instance, small iodinated resin particulates in powdered form make a sludge that is very difficult to manipulate and process. Additionally, using water necessitates implementation of at least one drying step, which increases the process time and manufacturing cost. Drying of small particulates is also very difficult since under drying processes the particulate will have a tendency to agglomerate in clumps requiring another particulate separating process post drying. The novel manufacturing process of the present invention eliminates much of the toxicological waste generated by the processes described in the prior art since no water containing iodine is generated and hence, no waste containing iodine are generated. Moreover, the process uses less raw materials (e.g., iodide) which would decrease manufacturing costs and produce a lesser quantity of hazardous waste.

Another significant advantage of the inventive manufacturing process is that the loss of iodine during manufacturing is considerably less than prior art methods. As described in the Examples, below, we compared the efficiency inventive manufacturing process with the currently used manufacturing process used to generate Triosyn® iodinated resin particulates at the same stoichiometric ratio. That is, the same ratio of solid resin to solid iodine/iodide was used. Following manufacturing, the percentage of iodine in the iodinated resin particulates was calculated. It was determined that the amount of iodine incorporated in the resin beads was significantly greater using the novel manufacturing process when compared with the older process used to produce Triosyn® particulates. Additionally, the amount of iodine less was less in the inventive process, than the older process, indicating that most iodine gets incorporated into the resin. Thus, the new method gives higher product yield and a higher percentage of iodine in the final product (% recovery). As such, the novel process is considerably more efficient in manipulation, material and cost analysis than prior art methods, translating to lower costs, greater microbiological efficiency and a better toxicological profile. Also, as discussed below, the manufacturing process of the present invention results in iodinated resin particulates considerably more efficacious than Triosyn® iodinated resin particulates produced using the current commercial process.

Yet another important advantage of the manufacturing process of the present invention is that it produces iodinated resin particulates that have a uniform quantity of iodine content. The current manufacturing process used to generate Triosyn® iodinated resin particulates is unable to produce particulates with uniform iodine content. We have found a large discrepancy in iodine content amongst individual particulates in a mixture of iodinated resin particulates generated by the prior methods of generating iodinated resin particulates. Using the novel methods described in the present invention, iodinated resin particulates with a high degree of uniformity are generated. Hence, when comparing particulates to particulates, the differences in iodine content on a wt/wt basis are negligible.

The uniformity of iodinated resin particulates produced by the process of the current invention has important consequences. When the particulates are incorporated into antimicrobial products such as a filters, wound dressings, medical diagnostic, polymeric extrusions, non-polymeric extrusions or paints/coatings, the performance of the product will be uniform. Contrast this with the prior art antimicrobial products where there may exist significant fluctuations of biocidal performance on different areas of the product owing to non-uniformity of iodine content of the iodinated resin particulates. Additionally, prior to the current invention, it was difficult to ensure that each antimicrobial product (e.g., filter) produced using iodinated resin particulates had consistent performance. The efficacy of the product is a function of the iodine content of the individual particulates, which was impossible to generate using prior art methods. Iodinated resin particulates generated in accordance with the present invention can be used in various products with the assurance that the performance of the individual products is essentially uniform.

We have performed a series of experiments designed to test the antimicrobial performance of iodinated resin particulates made by the current commercial process used to make Triosyn® iodinated resin and the novel process of the present invention. Several of the tests are described in the Experimental Section, below. We observed that when the two manufacturing process were designed to give the same total amount of iodine in the iodinated resin particulates (e.g., 45%), the particulates of the inventive process of the present application were substantially more efficacious than particulates produced by the current commercial process. Being that the total iodide content on the particulates produced by the two processes is essentially the same, we attribute this increased efficacy to the greater uniformity of iodine content from particulate to particulate in the iodinated resin produced by the new process.

Although the manufacturing process described above was used for the manufacturing of iodinated resin particulates, manufacture of other resin particulates may also be developed in accordance with the present invention. For example, in addition to using anionic exchange resins, other materials can be used (alone or in combination of). These materials include:
 a) cationic resins
 b) cellulose
 c) Polypropylene (PP)
 d) Polyethylene (PE) including high density polyethylene, linear low density polyethylene (LLDPE), ethylene copolymers (EVA and EMA)
 e) Nylon (all types)
 f) Polyamides
 g) polyester
 h) polymethylmethacrylate
 i) polyurethanes (PU)

Furthermore, in addition to using iodine, other active agents may be used either stand alone or in combination in accordance with the present invention. Examples of other active agents include chlorine, bromine, and other non-solid and or non-sublimating chemical agents. The process for generating particulates with these active agents would be similar to the process described for reacting iodine with an anionic resin, as described above.

Use of Iodinated Resins

The iodinated iodinated resin manufactured in accordance with the present invention (or other compounds as disclosed) can be used in various applications. For instance, the iodinated resins may be used in antimicrobial and antiviral products, decontaminates, and disinfectants. The iodinated resins may also be used to disinfect fluids containing microorganisms, such as fluids including air and water. The iodinated resins may also be used to disinfect biological fluids such as blood.

Additionally, the active resins manufactured in accordance with the present invention may be placed on a carrier component. The carrier component containing iodinated resin may be incorporated into a textile, nonwoven, or sterilization dressing.

Additionally, the active resins manufactured in accordance with the present invention may be embedded in a polymeric or non-polymeric structure to generate a mixture that can be applied as a coating or paint. For instance, the active resin particulates may be incorporated into a polymer and the resultant polymer/iodinated resin can be used to coat the surface of an elastomeric material, such as a glove, catheter or condom. To prepare the coating material, the active resin particulates are added to an aqueous dispersion of polymer. Preferred polymers include acrylonitrile-based polymers, polyurethanes, polyacrylics, hydrogel polymers and polyacrylic/polyurethane blends. After forming the polymer mixture, the elastomeric product (e.g., glove, condom or catheter) may be dipped into the mixture and dried. Alternatively, the polymeric mixture containing iodinated resin particulates may be sprayed onto the elastomeric material.

One preferred embodiment involves using iodinated resins produced in accordance with the manufacturing process of the present invent in antimicrobial products. Iodinated resins exert a toxic effect on a large array of different microorganisms and hence, have widespread utility. Iodinated resin particulates of the present invention may be used in wound dressings, blood transfusion devices, aerosols, textiles, filters, polymeric extrusions, non-polymeric extrusions, wipes and paints/coatings.

The iodinated resin particulates of the present invention are particularly useful to be used in filters. U.S. Patent Application No. 2006/0144403, which is incorporated by reference, describes various methods of incorporating iodinated resin particulates into nonwoven materials or compressible materials to generate antimicrobial filters. The novel iodinated resin particulates of the present invention, when incorporated into a filter, have consistent biological performance throughout the filtering material owing to the uniformity of iodine content amongst the iodinated resin particulates. Hence, the filter media is capabable of eradicating toxins more efficiently than prior art solutions. Examples of filter media used in accordance with the present invention include facemasks and HVAC. The filter media, preferably in the form of a compressible material, may be formed into a compressible gasket that is configured to sit on the periphery of a facemask. In use, the compressible gasket sits between the facemask and the user's face, creating a breathable closure. The compressible gasket containing iodinated resin particulates formed by methods in accordance with the present invention is capable of devitalizing microorganisms passing through it.

Filters using the iodinated resin particulates of the present invention can be prepared using methods described in U.S. Patent Application No. 2006/0144403. One such method involves making use of a meltblown system where the desired iodinated resin is provided in a cloud at the location closest to the extrusion point of polypropylene fibers. The cloud of iodinated resin envelops the extruded fibers exiting a spinneret. thus the iodinated resin becomes physically entrapped between the fibers on the collecting web.

Alternatively, the iodinated resin particulates of the present invention may be incorporated directly into the fibers of the nonwoven filter. Methods of incorporating an iodinated resin into a nonwoven material are also known in the art. Generally, the iodinated resin is blended with the polymer prior to extrusion, so that it is present throughout the polymer. Upon solidification of the polymer, the iodinated resin is dispersed throughout the resultant fiber. Iodine may diffuse to the surface of the nonwoven, where it exerts is toxic effect on the microorganism/toxin. Also, fibers containing the iodinated resin can be generated by extrusion and coolent on spools, which can further by air entanglement, water entanglement and/or needle punch.

Examples of Manufacturing Process

A study was conducted comparing the properties and biological performance of iodinated resins particulates produced in accordance with the present invention and iodinated resin particulates produced by the commercial process currently used to produce Triosyn® iodinated resin particulates. The older commercial manufacturing and new manufacturing process performed in accordance with the present invention are described below.

A.) Process to Produce Triosyn® Iodinated Resin Particulates Based on the Current Commercial Manufacturing Process
 i. Create a potassium triiodide ($KI_3^-$) slurry:
  a. Weigh out 0.648 kg elemental iodine ($I_2$; prilled USP grade)
  b. Weigh out 0.261 kg potassium iodide (KI)
  c. Add $I_2$ to the KI
  d. Add 0.066 kg of water (demineralized) to the $I_2$/KI mix
  e. Mix all components until well blended
 ii. Weigh out 0.4 kg of anionic Amberlite resin (500 μm; on a dry weight base)
 iii. Add the anionic resin to the $KI_3^-$ slurry.
 iv. Mix anionic resin and $KI_3^-$ slurry for a minimum of 30 minutes.

v. Heat the mixture for 10 minutes at a pressure of 15 psi (approximately 105-110° C.).
vi. When heating is complete, cool mixture.
vii. Rinse mixture with water to remove excess $I_2$ and $KI_3^-$ from the iodinated resin.
viii. Dry iodinated resin.
ix. Recover iodinated resin beads
x. Micronize iodinated resin beads to produce iodinated resin particulates with particle sizes ranging from 3 microns to 5.83 microns.

B.) Process to Produce Triosyn® Iodinated Resin Particulates Based on Manufacturing Process of the Current Invention
i. Obtain micronized anionic Amberlite resin (no iodine present) by using a milling process to micronize.
ii. Weigh out 0.85 kg of jet milled anionic (dry wet base) resin ranging in size from about 0.1 to 300 microns.
iii. Weigh out 1.33 kg of the micronized iodine.
iv. Put the solid mixture in a corrosion resistant vessel and cap it.
v. Place container in a rotary mixer for a time period of 30 minutes.
vi. Once mixing is complete, place the container in high pressure/high temperature heathing vessel for heating. Heat at 110° C. at pressures of 15 psi for 15 minutes. When heating is complete, remove the container from the cooker and cool.
vii. Once cooled, pack and store the final iodinated resin product.

A comparison of components for the two processes described above are outlined in the following Table 1 below. The % $I_2$ initially added was calculated by dividing the amount of iodine initially used in the process with the total amount of iodine and milled dried anionic resin (on a dry basis) used in the process. The % $I_2$ in the final product was determined using the percent recovery method. The Percent Recovery method determines the concentration of elemental iodine ($I_2$) in the Triosyn resin or particulate. The iodine contained in resin/particulates neutralized by the addition of 0.1N sodium thiosulfate in the following reaction:

$$I_2 + 2S_2O_3^{-2} \rightarrow 2I^- + S_4O_6^{-2}$$

After the reaction is brought to completion, the excess sodium thiosulfate in solution is titrated using 0.1N iodine solution. The volume of iodine solution used in the reverse titration enables the determination of iodine content in the resin/particulate through mathematical calculations.

TABLE 1

Comparison of iodinated resin produced by commercial manufacturing process (old process) and inventive process (new process).

|  | Old Process | New Process |
| --- | --- | --- |
| Anionic resin (Kg) | 0.4 | 0.85 |
| Potassium Iodide (KI) | 0.26117 | 0 |
| Iodine ($I_2$) | 0.64862 | 1.33 |
| Water (demineralized) | 0.06601 | 0 |
| Total weight of all components (g) | 1.375 | 2.18 |
| % $I_2$ initially added | 62% | 61% |
| % $I_2$ in the final Product | 44% | 47% |
| Iodinated final Product (Kg) | 1.02172 | 2.0615 |

Table 1 indicates that the new inventive process produces a higher percentage of iodine in the iodinated resin, despite starting with the same ratio of iodine to iodinated resin as the current commercial process (old process). Additionally, the overall yield of the final iodinated resin product is greater in the new process than in the old process. Moreover, the old commercial process wastes a significant amount of iodine whereas the new inventive process loses only minimal iodide. Hence, the new process is considerably more environmentally friendly than the current commercial process.

Biological Testing

The iodinated resin produce in accordance with the present invention was tested for biological activity. *Klebsellia pneumonia*, a gram-negative microorganism, was used as the test organism An ASTM microbiological method was use to quantitatively determine the ability of the iodinated resin to deactivate the microorganism.

AATCC Microbiological Method:
i. Test articles (1"×1") are placed in individual sterile 50 mm Petri dishes.
ii. A microbial suspension is prepared in sterile agar slurry (8.5 g/L NaCl, 3 g/L Agar) so as to provide a titer of approximately 108 PFU or CFU per ml, respectively.
iii. The agar slurry microbial suspension is vortexed immediately prior to inoculation to assure uniform distribution of the challenge microorganism.
iv. Each swatch is inoculated with 0.1 ml of the microbial suspension. The Petri dishes are incubated at room temperature for pre-determined contact time(s).
v. Following the specified contact time, each swatch is aseptically transferred into a sterile 50 ml conical tube containing 10 ml of sterile PBS-TT (0.5% Tween and 0.1% sodium thiosulfate) and the tube is vortexed to allow complete neutralization of the antimicrobial ingredient and release the microorganisms from the test article.
vi. The solution is then collected and serial dilutions are plated on Petri dishes containing the appropriate growth medium using standard microbiology techniques.
vii. The degree of antibacterial activity of a given material for a specific contact time, expressed as % reduction, is calculated as follows.

% Reduction=100(*C*–*A*)/*C*

Where:
C=the number of bacteria recovered from the inoculated untreated control specimen swatches immediately after inoculation (at T=0 contact time)
A=the number of bacteria recovered from the inoculated treated test specimen swatches incubated for the specified contact time Preparation of the iodinated resin was conducted similar to as described above. The iodinated resin powder made in accordance with the new inventive process used solid resin and solid iodine with a percent iodine in the initial manufacturing preparation of 65.7%. The iodinated resin made in accordance with the old commercial process powder contained approximately 62% iodine in the initial mixture. The results displayed in Table 2 indicate that not only the microbiological performance results against *Klebsellia* are vastly superior for the new manufacturing method and the product it generates but also that with initial similar weight to weight chemical mixture preparation we obtain a superior iodine containing end product with the new manufacturing method.

TABLE 2

Biological results comparing iodinated resins manufactured by different processes.

| Resin | % I$_2$ (wt/wt) in the initial mixture to the final product amount | I$_2$ % Recovery of end product content | Log Reduction† |
|---|---|---|---|
| New Process | 65.7% | 60% | >5.53 |
| Old Process | 61.9% | 44% | 0.27 |

Method Detection Level = 50CFU
†Modified microbiology procedure: AATCC 100
Results taken at a 1 minute contact time A similar experiment was conducted but a smaller amount of iodine was used in the initial mixture. Again, results indicate that we a superior % iodine (47% for new process) and 44% (for old process). When testing against *Klebsellia* at a contact time of 7 minutes, the iodinated resin generated with the novel manufacturing method yields a superior microbiocidal performance by approximately 2.5 Logs at 7 minutes contact time.

TABLE 3

Biological results comparing iodinated resins manufactured by different processes.

| Resin | % I$_2$ (wt/wt) in the initial mixture to the final product amount | I$_2$ % Recovery of end product content | Log Reduction† |
|---|---|---|---|
| New Process | 61% | 47% | 3.95 |
| Old Process | 61.9% | 44% | 1.48 |

Method Detection Level = 50CFU
†Modified microbiology procedure: AATCC 100
Results taken at a 7 minute contact time

The invention claimed is:

1. A manufacturing process for producing an iodinated resin comprising:
   a. providing a quantity of crystalline iodine;
   b. providing a quantity of milled dry non-activated resin;
   c. mixing the iodine and the milled dry resin in a vessel for a period of time sufficient to form an intimate non-aqueous mixture;
   d. placing the vessel with said mixture in a high pressure/high temperature heating vessel for a period of time sufficient to allow the iodine to absorb or become impregnated in said resin, thereby providing an iodinated resin;
   e. recovering the iodinated resin.

2. The process according to claim 1, wherein the time period for mixing is from about 10 minutes to about 20 hours.

3. The process according to claim 1, wherein the mixture in the pressure cooker is heated from about 65° C. to about 250° C. at a pressure of about 1 psi to about 300 psi.

4. The process according to claim 3, wherein the mixture in the pressure cooker is heated from about 100° C. to about 130° C. at a pressure of from about 10 psi to about 30 psi.

5. The process according to claim 1, wherein the milled dry resin is an anionic resin.

6. The process according to claim 5, wherein the milled dry resin is a strong-base or weak base ion-exchange resin.

7. The process according to claim 6, wherein the resin is selected from the group consisting of Amberlite IRA-401 S, Amberlite IR-400 (Cl$^-$), Amberlite IR-400 (OH$^-$), and Amberlite IR-402 (Cl$^-$).

8. The process according to claim 1, wherein the milled dry resin is selected from the group consisting of cellulose polypropylene, polyethylene, polyamides, polystyrene, polymethylmethacrylate, and polyurethanes.

9. The process according to claim 1, wherein the ratio of the micronized iodide to the milled dry resin is 0.3 to 3.0 on a weight/weight basis.

10. A manufacturing process for producing a mixture of iodinated resin particulates, comprising:
   a. providing a quantity of crystalline iodine;
   b. providing a quantity of milled dry non-activated resin, wherein the milled dry resin is an anionic resin;
   c. mixing the iodine and the milled dry anionic resin in a vessel for a period of time sufficient to form an intimate non-aqueous mixture;
   d. placing the vessel with said mixture in a pressure cooker for a period of time sufficient to allow the iodine to absorb or become impregnated in said resin, thereby providing an iodinated resin;
   e. recovering the iodinated resin;
   wherein the mixture of iodinated resin particulates have a particle size substantially in the range of 0.1-300 microns and wherein all the particulates have substantially the same weight percentage of iodine.

11. The process according to claim 10, wherein the weight percentage of iodine in said particulates is in a range from about 0.3 to 3.0 on a weight/weight basis.

12. An antimicrobial filter comprising an extrudable polymer and plurality of iodinated resin particulates formed according to claim 1 and incorporated into said filter, wherein the iodinated resin particulates have a particle size substantially in the range of 0.1-300 microns and wherein the individual particulates have substantially the same weight percentage of iodine.

13. The antimicrobial filter of claim 12, wherein the antimicrobial filter is a nonwoven or compressible material.

14. The antimicrobial filter of claim 13, wherein the nonwoven or compressible material is configured into the shape of a facemask.

15. The antimicrobial filter of claim 13, wherein the nonwoven or compressible material is a gasket, said gasket configured to sit on the periphery of a facemask.

16. An antimicrobial coating or sterilization dressing comprising iodinated resin particulates formed according to claim 1.

17. A antimicrobial coating for an elastomeric material, said coating comprising a polymer and a plurality of iodinated resin particulates formed according to claim 1 and incorporated into said polymer, wherein the iodinated resin particulates have a particle size substantially in the range of 0.1-300 microns and wherein the individual particulates have substantially the same weight percentage of iodine.

18. The antimicrobial coating of claim 17, wherein the elastomeric material is selected from the group consisting of a glove, catheter or condom.

19. The elastomeric coating of claim 17, wherein the polymer is selected from the group consisting of acrylonitrile-based polymers, polyurethanes, polyacrylics, hydrogel polymers and polyacrylic/polyurethane blends.

* * * * *

UNITED STATES PATENT AND TRADEMARK OFFICE
CERTIFICATE OF CORRECTION

PATENT NO. : 8,071,713 B2
APPLICATION NO. : 12/586504
DATED : December 6, 2011
INVENTOR(S) : Pierre J. Messier et al.

It is certified that error appears in the above-identified patent and that said Letters Patent is hereby corrected as shown below:

IN THE PATENT:

Column 2, Line 40 now reads: "with requires" ..... SHOULD READ: "which requires"

Column 3, Line 26 now reads: "iodinated rein" ..... SHOULD READ: "iodinated resin"

Column 5, Line 27 now reads: "iodinated rein particulates" ..... SHOULD READ: "iodinated resin particulates"

Column 7, Line 31 now reads: "the iodinated iodinated resin" ..... SHOULD READ: "the iodinated resin"

Column 7, Line 64 now reads: "of the present invent" ..... SHOULD READ: "of the present invention"

Column 8, Line 38 now reads: "exerts is toxic effect" ..... SHOULD READ: "exerts its toxic effect"

Column 9, Line 23 now reads: "temperature heathing vessel" ..... SHOULD READ: "temperature heating vessel"

Column 10, Line 15 now reads: "was use" ..... SHOULD READ: "was used"

Signed and Sealed this
Sixteenth Day of October, 2012

David J. Kappos
*Director of the United States Patent and Trademark Office*